US008659287B2

(12) United States Patent
Ukai et al.

(10) Patent No.: US 8,659,287 B2
(45) Date of Patent: *Feb. 25, 2014

(54) HARD PARTICLE CONCENTRATION DETECTING METHOD

(75) Inventors: Hidemi Ukai, Tokyo (JP); Takashi Fujii, Aioi (JP)

(73) Assignees: IHI Corporation, Tokyo (JP); Diesel United, Ltd., Tokyo (JP)

( * ) Notice: Subject to any disclaimer, the term of this patent is extended or adjusted under 35 U.S.C. 154(b) by 249 days.

This patent is subject to a terminal disclaimer.

(21) Appl. No.: 13/256,119

(22) PCT Filed: Mar. 10, 2010

(86) PCT No.: PCT/JP2010/001697
§ 371 (c)(1),
(2), (4) Date: Sep. 12, 2011

(87) PCT Pub. No.: WO2010/103824
PCT Pub. Date: Sep. 16, 2010

(65) Prior Publication Data
US 2012/0001619 A1      Jan. 5, 2012

(30) Foreign Application Priority Data

Mar. 12, 2009  (JP) .................................. 2009-059469
Dec. 24, 2009  (JP) .................................. 2009-291799

(51) Int. Cl.
*G01N 27/74*      (2006.01)
*G01R 33/12*      (2006.01)

(52) U.S. Cl.
USPC ........................................................ 324/204

(58) Field of Classification Search
USPC ........................................................ 324/204
See application file for complete search history.

(56) References Cited

U.S. PATENT DOCUMENTS

| 5,790,246 A | 8/1998 | Kuhnell et al. |
| 8,037,740 B2 | 10/2011 | Fujii |
| 2009/0189599 A1 | 7/2009 | Fujii et al. |

FOREIGN PATENT DOCUMENTS

| JP | 59 54956 | 3/1984 |
| JP | 63 300963 | 12/1988 |
| JP | 11 153541 | 6/1999 |
| JP | 2001 503848 | 3/2001 |
| JP | 2008 8885 | 1/2008 |

OTHER PUBLICATIONS

Fujii, T., "New Technology for Condition Monitoring of Large 2-stroke Diesel Engine and Its Application," Marine Engineering, vol. 42, No. 4, pp. 79-82, (Jul. 1, 2007), document not in english.
International Search Report Issued Jun. 8, 2010 in PCT/JP10/001697 Filed Mar. 10, 2010.
U.S. Appl. No. 13/514,095, filed Jun. 6, 2012, Ukai et al.

*Primary Examiner* — Reena Aurora
(74) *Attorney, Agent, or Firm* — Oblon, Spivak, McClelland, Maier & Neustadt, L.L.P.

(57) ABSTRACT

Magnetic and counterpart members are immersed in a liquid which may include hard particles. At least one of the members is moved while pressed to the other member. The magnetic member is worn by hard particles in the liquid to produce magnetic particles in the liquid. A concentration of the magnetic particles produced is measured and is converted into a concentration of hard particles in the liquid on the basis of a calibration line representing a correlation measured in advance between the concentrations of the magnetic particles and of the hard particles in the liquid. Thus, the concentration of the hard particles in the liquid is detected.

2 Claims, 12 Drawing Sheets

RELATIONSHIP BETWEEN GRINDING TIME PERIOD
AND CONCENTRATION OF MAGNETIC PARTICLES (Fe)

CALIBRATION LINE SHOWING CORRELATION BETWEEN CONCENTRATIONS OF HARD PARTICLES AND OF MAGNETIC PARTICLES

HARD PARTICLE CONCENTRATION DETECTING METHOD

TECHNICAL FIELD

The invention relates to a concentration detecting method for hard particles in a liquid.

BACKGROUND ART

Generally mixed in a liquid such as bunker C, which is a main fuel for a marine diesel engine, are alumina, silica, carbon or other hard particles as residue in fluid catalytic cracking (FCC) for petroleum refinery.

Excessive inflow of such hard particles into the engine with a piston ring, a cylinder liner and the like may cause adverse effects such as degraded sliding, seizing-up and mechanical wear. Thus, every time fuel is replenished, a ship management company samples and chemically analyzes the fuel to quantitatively grasp the hard particles in the fuel. When fuel with hard particles of not less than a stipulated concentration is replenished to a ship, the fact is notified of to the ship's crew to call their attention.

Conventionally, when hard particles in fuel are to be detected, sampled fuel is filtered through a filter or the like and a residue is microscopically observed or quantitatively analyzed to detect hard particles.

State-of-the-art technology with respect to a hard particle concentration detecting method is shown, for example, in Patent Literature 1.

CITATION LIST

Patent Literature

[Patent Literature 1] JP 11-153541A

SUMMARY OF INVENTION

Technical Problems

However, any conventional hard particle concentration detecting method require a specific number of days until an analyzed result is reported to the ship's crew. Therefore, when the fuel requires to be used pending the analysis result, a problem arises that adverse effects on the driving engine cannot be preliminarily prevented. A large amount of hard particles may be suddenly supplied to the engine when a hard particle-including contaminant is precipitated to increase the concentration of the hard particles in the fuel during storage or when malfunction of a filter, a centrifugal separation cleaner or the like occurs in a fuel treatment system from a fuel tank to an inlet of the engine. Thus, continuous and quantitative grasp of the hard particles in the fuel is demanded.

There is also a problem that alumina, silica or other hard particles, which have no remarkable features in magnetism and in electric conductivity, are difficult to magnetically or electrically detect. There is further a problem that the hard particles, which are chemically stable, are difficult to detect utilizing a chemical reaction. There is still further a problem that the bunker C or the like liquid, which is opaque and highly viscous and includes various sludge or other hard particles in addition to the alumina and silica particles, cannot be sufficiently dealt with using optical determination as described in Patent Literature 1.

The invention was made in view of the above and has its object to provide a hard particle concentration detecting method which quickly and quantitatively grasps hard particles in a liquid.

Solution to Problems

A hard particle concentration detecting method of the invention comprises the steps of immersing magnetic and counterpart members in a liquid which may include hard particles, moving at least one of the members while the member is pressed to the other member, wearing the magnetic member by hard particles in the liquid to produce magnetic particles in the sample liquid, measuring a concentration of the magnetic particles produced, and converting the measured concentration of the magnetic particles into a concentration of hard particles in the liquid on the basis of a calibration line representing a correlation measured in advance between the concentrations of the magnetic particles and of the hard particles in the liquid to thereby detect the concentration of the hard particles in the liquid.

In the hard particle concentration detecting method of the invention, it is preferable that said at least one of magnetic and counterpart members is moved while pressed to the other member and with the hard particles in the liquid being between the members.

Advantageous Effects of Invention

According to the hard particle concentration detecting method of the invention, presence of the hard particles in the liquid is used to wear the magnetic material to thereby produce the magnetic particles in the liquid; and the concentration of the magnetic particles produced is measured, and is converted into the concentration of the hard particles in the liquid by use of the calibration line to thereby detect the concentration of the hard particles in the liquid. As a result, the hard particles in the liquid can be quickly and quantitatively grasped. When the liquid is an oil, the states can be prevented where untested fuel is used and where a large amount of hard particles are suddenly supplied to a driving engine, thereby suppressing any adverse effect on the driving engine. The fact that the concentration of the hard particles is indirectly detected using the magnetic particles produced by the wearing of the magnetic member brings about excellent effects that there is no necessity of any operation and process for directly detecting the hard particles through physical or chemical treatment of the liquid itself and that favorably the hard particles in the liquid can be quickly and quantitatively grasped.

DESCRIPTION OF EMBODIMENT

Figure 1:
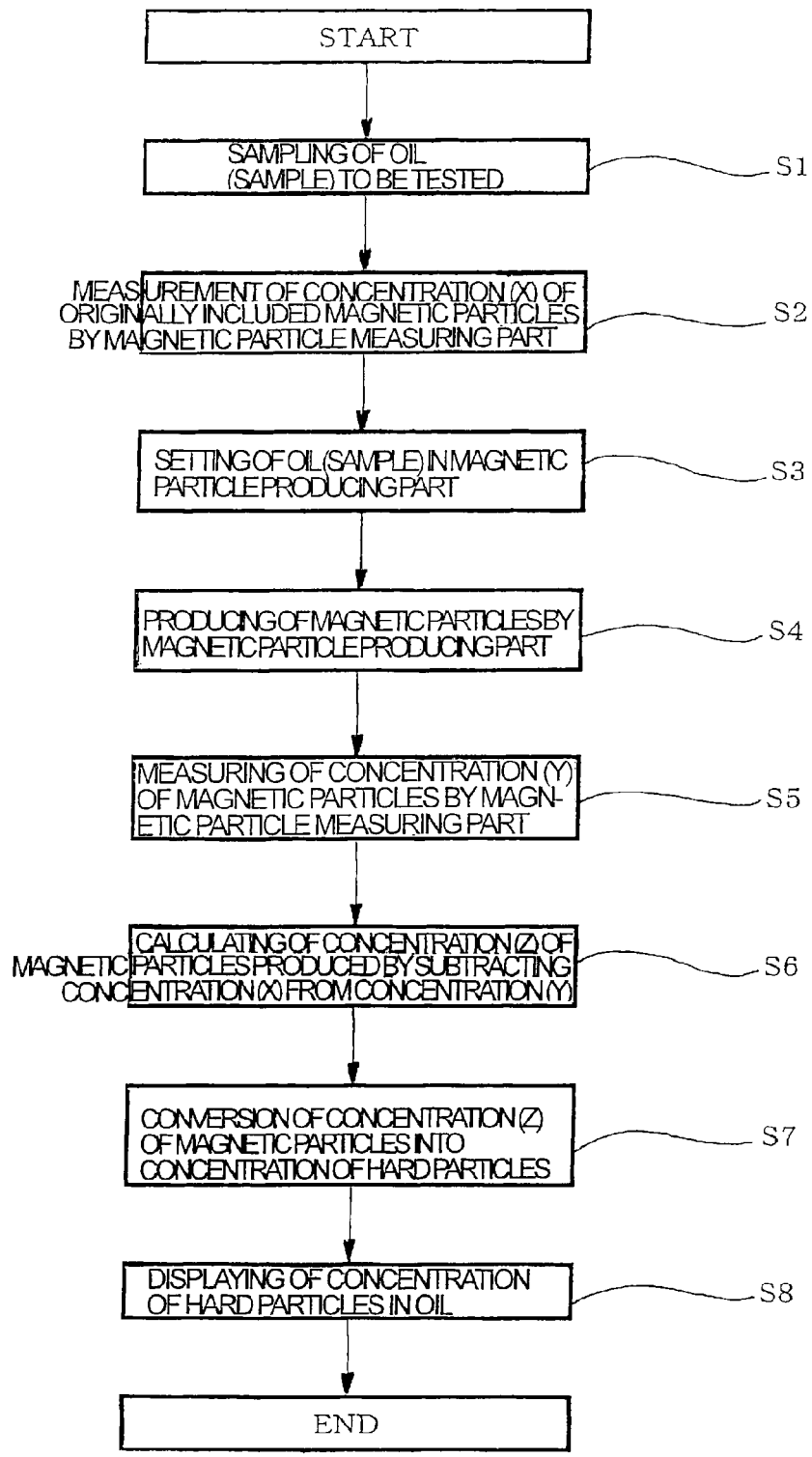
FIG. 1 is a flowchart of a process procedure of a hard particle concentration detecting method of the invention.
Figure 2:
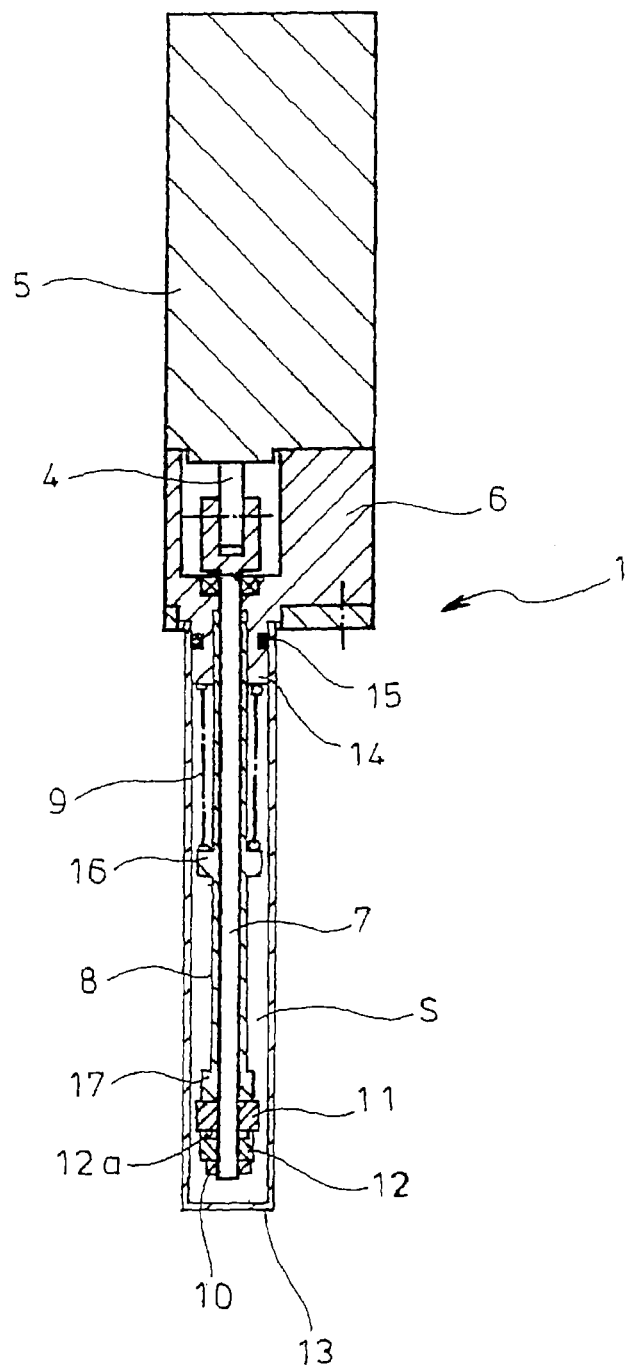
FIG. 2 is a general conceptual view showing a magnetic particle producing part in the hard particle concentration detecting method of the invention.
Figure 3:
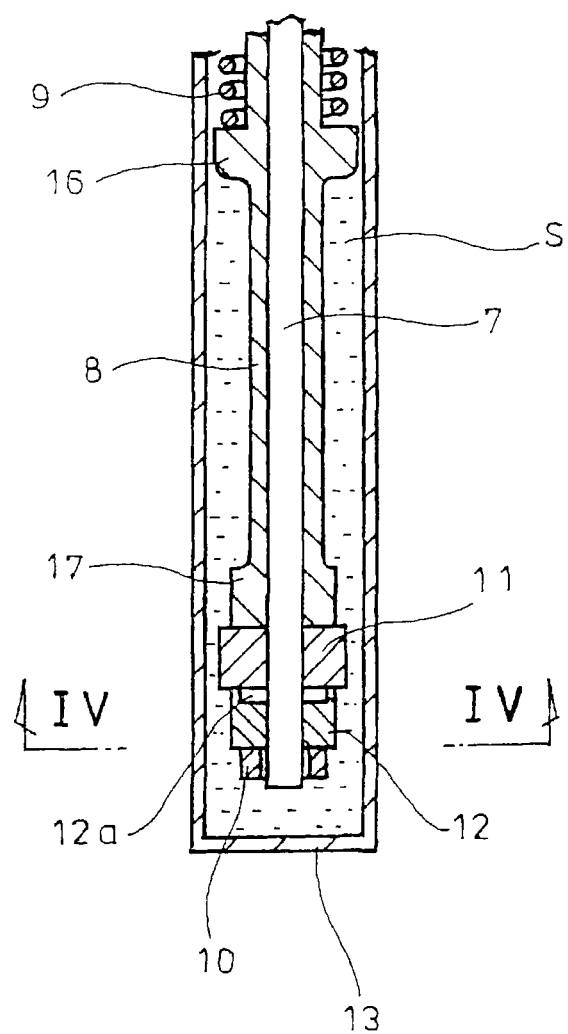
FIG. 3 is a conceptual view showing, in enlarged scale, magnetic and counterpart members in the magnetic particle producing part of FIG. 2.
Figure 4:
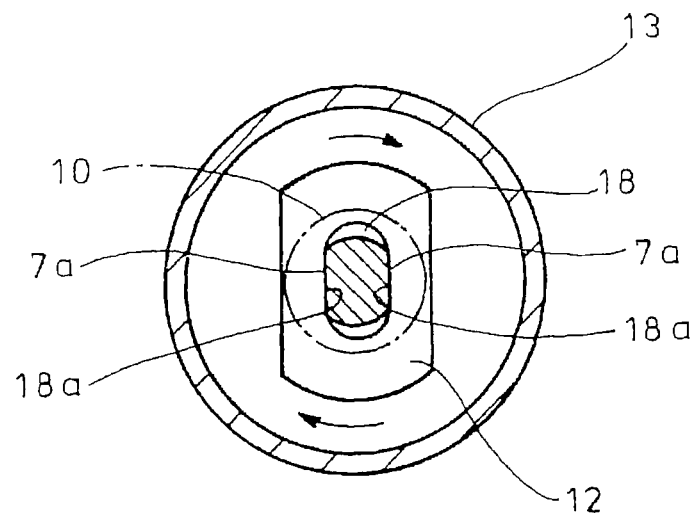
FIG. 4 is a view looking in the direction of arrows IV in FIG. 3.

An embodiment of a hard particle concentration detecting method according to the invention will be described with reference to FIGS. 1 to 12.

The embodiment provides a magnetic particle producing part (magnetic powder producing part) 1 for production of magnetic particles (magnetic powder) in a liquid, a magnetic particle measuring part 2 (see FIGS. 6 to 8) for measurement of a concentration of the magnetic particles in the liquid and a control part 3 (see FIGS. 6 and 7) for processing of the concentration of the magnetic particles. The embodiment will be described with respect to a case where the liquid is an oil.

The magnetic particle producing part 1 comprises a motor or other drive 5 with a rotating shaft 4 therebeneath, a holder 6 on the drive 5 to surround the shaft 4, a rod 7 connected to the shaft 4 to extend downward and outward of the holder 6, a sleeve 8 supported by the holder 6 and fitted over the rod 7, a spring or other resilient member 9 biasing the sleeve 8 downward and wear-plate counterpart and plate-like magnetic members 11 and 12 arranged underneath the sleeve 8 using a nut or other fixing member 10.

The drive 5 and the holder 6 are fixed to a pedestal (not shown) to expose the rod 7, the sleeve 8 and the like downward. The holder 6 has a downward protrusion 14 over which a test tube or other container 13 with a fuel or other oil S therein can be fitted. The protrusion 14 has a circumferential groove with an O-ring 15 fitted therein.

The rod 7 is of a length accommodable in the container 13 together with the members 8, 9, 11 and 12 when the container 13 is arranged on the holder 6, and is adapted to be rotated by the drive 5. The rod 7 has a lower portion circumferentially oppositely and planarly cut out to provide opposite side faces 7a (see FIG. 4).

The sleeve 8 is formed with an upper support 16 for support of a lower portion of the resilient member 9 as well as a lower support 17 abutting on the counterpart member 11. The resilient member 9 is supported by the protrusion 14 on the holder 6 and biases the counterpart member 11 downward through the sleeve 8 to thereby press the member 11 against the magnetic member 12. Preferably, the pressure to the members 11 and 12 is adjusted by exchanging the spring or other resilient member 9.

The counterpart member 11 has a bore (not shown) for passing of the rod 7 therethrough and is adapted so as not to follow the rotation of the rod 7 whereas the magnetic member 12 has a bore 18 (see FIG. 4) for passing of the rod 7 therethrough to provide opposite planar portions 18a on which the side faces 7a of the rod 7 lower portion can abut so that the magnetic member 12 follows the rotation of the rod 7. The magnetic member 12 is made of an iron-based or other material having magnetism. The counterpart member 11 is made of carbon steel or other material harder and less wearable than the magnetic member 12. Either of the members 11 and 12 (the member 12 in FIGS. 2 and 3) is formed with a groove 12a which faces the other member. When the magnetic member 12 is rotated with hard particles being between the members 11 and 12, the magnetic member 12 is scraped off into abrasive wear by the hard particles. The material of the magnetic member 12 is not limited to iron and may be any, provided that magnetic particles (magnetic powder) with a required diameter may be produced due to the wearing. The material of the counterpart member 11 may be different from or the same as that of the magnetic member 12, provided that the magnetic particles may be produced from the magnetic member 12. The magnetic and counterpart members 12 and 11 may be arranged with their positions exchanged.

Figure 5A:
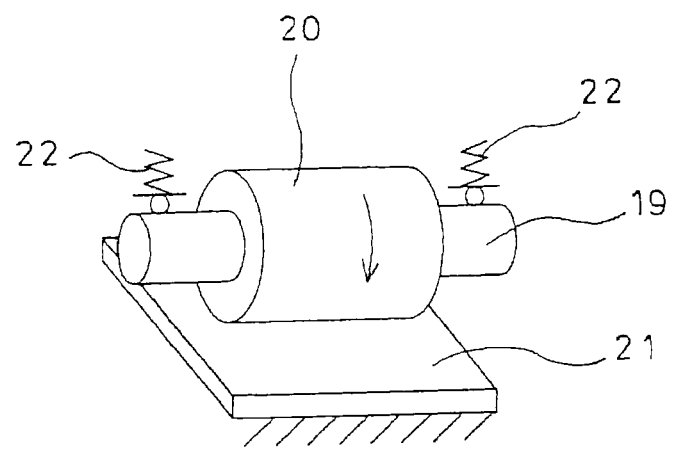
FIG. 5a is a conceptual view showing magnetic and counterpart members in an alternative magnetic particle producing part.

An alternative example of the magnetic particle producing part 1 may be employed which has components different from the members 12 and 11 and the like. More specifically, it comprises, as shown in FIG. 5a, a shaft 19 rotated by a drive (not shown), a roller 20 positioned centrally over the shaft 19, a plate 21 fixed to a stationary member (not shown) and abutting on the roller 20 and springs or other resilient members 22 biasing the shaft 19 to press the roller 20 onto the plate 21. Either of the roller 20 and the plate 21 is a magnetic member and the other is a counterpart member.

Figure 5B:
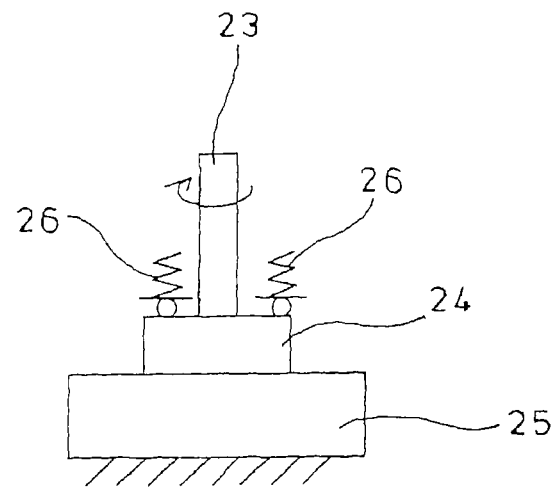
FIG. 5b is a conceptual view showing magnetic and counterpart members in a further alternative magnetic particle producing part.

A further alternative example may be employed which comprises, as shown in FIG. 5b, a shaft 23 rotated by a drive (not shown), a rotating plate 24 positioned on a tip of the shaft 23, a plate 25 fixed to a stationary member (not shown) and abutting on a bottom of the rotating plate 24 and springs or other resilient members 26 pressing the rotating plate 24 against the plate 25. Either of the plates 24 and 25 is a magnetic member and the other is a counterpart member.

Figure 5C:
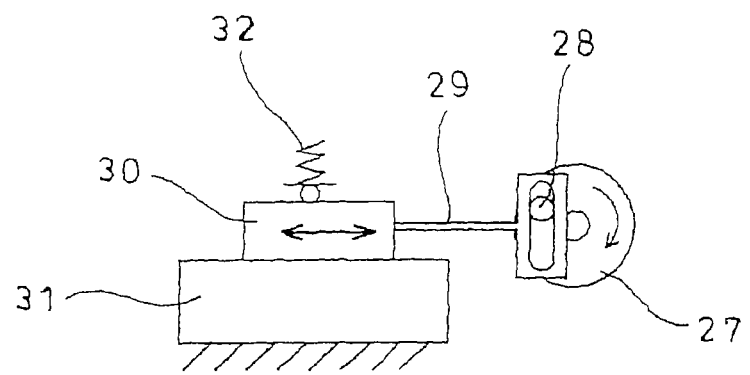
FIG. 5c is a conceptual view showing magnetic and counterpart members in a still further alternative magnetic particle producing part.

A still further alternative example may be employed which comprises, as shown in FIG. 5c, an eccentric pin 28 rotated by a drive 27, a connecting member 29 to convert a motion of the eccentric pin 28 into a reciprocating motion, a reciprocating plate 30 connected to the connecting member 29, a plate 31 fixed to a stationary member (not shown) and abutting on a bottom of the reciprocating plate 30 and a spring or other resilient member 32 to press the reciprocating plate 30 against the plate 31. Either of the plates 30 and 31 is a magnetic member and the other is a counterpart member.

Next, an example of the magnetic particle measuring part 2 will be described though it is not especially limited in construction, providing a concentration of the magnetic particles can be measured in ppm. As shown in FIGS. 6 to 10, the exemplary magnetic particle measuring part 2 comprises a flow path L of an oil S which may include magnetic particles. The flow path L is provided with a fluid lead-out/lead-in guide unit 33 and a detecting unit 34. The detecting unit 34 is connected to a signal processing unit 35 which in turn is connected to a concentration measuring unit 36 for conversion of a signal from the signal processing unit 35 into a concentration of the magnetic particles.

The lead-out/lead-in guide unit 33 comprises a cylindrical detector body 38 opened at 37 to the flow path L, a piston 39 which slides inside the detector body 38 for guided lead-out/lead-in of the oil S, a drive or rotating body 40 (see FIG. 8) for forward/backward movement of the piston 39 and coils 41 of the detecting unit 34 arranged on a circumference of the detector body 38. The flow path L may be a pipe, a tube or any other, provided that the oil S flows therethrough.

The coils 41 of the detecting unit 34 are two exciting coils 41a wound in opposite directions to each other and connected in series and a detection coil (output coil) 41b arranged between and adjacent to the coils 41a. The detection coil 41b is adapted to generate an output signal indicative of an AC voltage (exciting voltage) when the AC voltage is applied to the exciting coils 41a. The exciting and detection coils 41a and 41b are adjusted to have substantially uniform mutual inductance by adjusting wound number and distance of the coils 41. The exciting and detection coils 41a and 41b have no limitation in their numbers.

Figure 7:
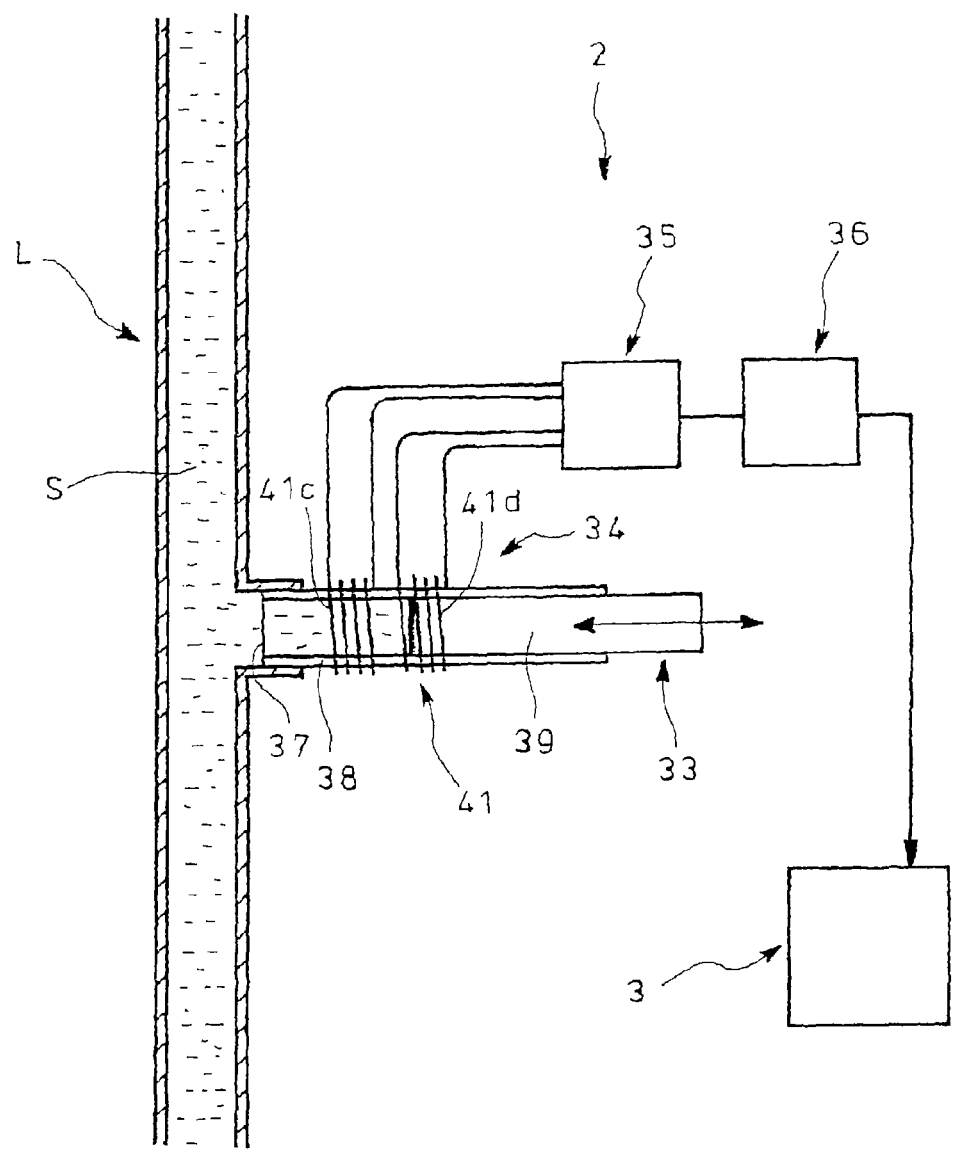
FIG. 7 is a general conceptual view showing an alternative example of the magnetic particle measuring part in the hard particle concentration detecting method of the invention.

Alternatively, as shown in FIG. 7, the coils 41 of the detecting unit 34 may be an exciting coil 41c and a detection coil (output coil) 41d arranged adjacent thereto. Also in this case, the detection coil 41d is adapted to generate an output signal indicative of an AC voltage (exciting voltage) when the AC voltage is applied to the exciting coil 41c. It is adjusted such that the output signal indicative of the AC voltage (exciting voltage) in the detection coil 41d is small when no magnetic particles are detected.

Figure 8:
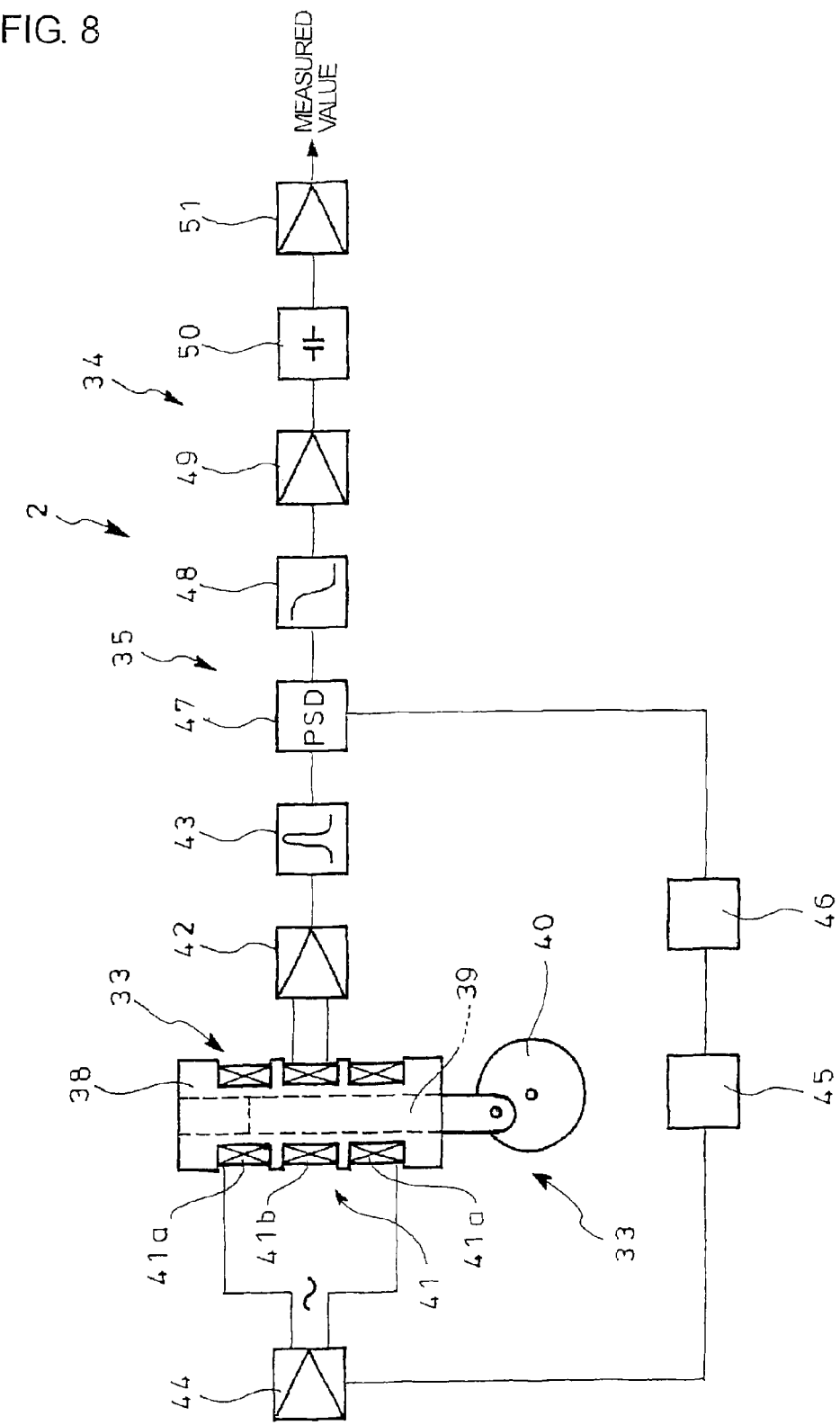
FIG. 8 is a block diagram showing a configuration of a signal processing unit in the magnetic particle measuring part.

As shown in FIG. 8, in order to acquire detection or corrective detection signal of the magnetic particles from the output signal of the detection coil 41b, the signal processing unit 35 comprises an amplifier circuit 42 connected to the coil 41b to amplify a feeble waveform signal, a band-pass filter 43 connected to the circuit 42 to remove noises of the waveform signal in a predetermined range, a sine wave oscillating circuit 44 connected to the coils 41a to acquire a sine wave for excitation, a phase circuit 45 connected to the circuit 44 to shift a phase of the sine wave and an edge-trigger circuit 46 connected to the circuit 45 to convert the sine wave into a rectangular wave.

It is preferable that, upon setting or adjustment and with no magnetic particles being detected, the phase circuit 45 shifts the phase by 10°-170°, preferably by 45°-135°, and further preferably by about 90°. The phase circuit 45 may be alternatively positioned between the band-pass filter 43 and a signal processor 47 to shift not the phase of the reference signal, but the phases of the detection or corrective detection signal of the magnetic particles.

The signal processing unit 35 further comprises the signal processor 47 connected to the band-pass filter 43 and to the edge-trigger circuit 46, a low-pass filter 48 connected to the processor 47 to convert the output signal into a DC voltage signal, an amplifier 49 connected to the filter 48 to amplify the DC voltage signal, an AC signal transmitting circuit 50 connected to the amplifier 49 to transmit only an amount varied of the DC voltage signal by the guided lead-out/lead-in of the detection fluid and an amplifier 51 connected to the circuit 50. The signal processor 47 is preferably a lock-in amplifier; however, it may be any, provided that it can measure variation in phase difference.

Figure 6:
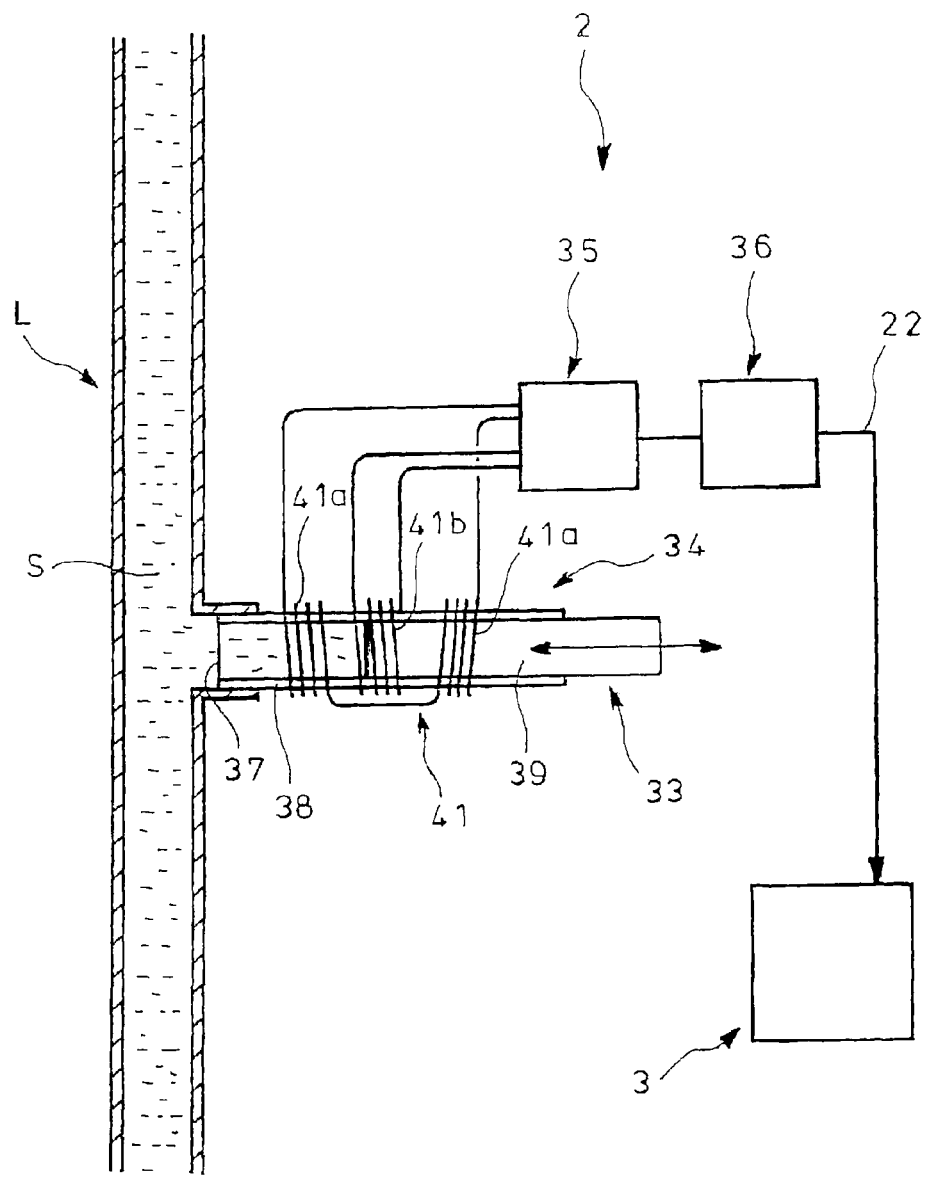
FIG. 6 is a general conceptual view showing an example of a magnetic particle measuring part in the hard particle concentration detecting method of the invention.

The amplifier 51 of the signal processing unit 35 is connected to the concentration measuring unit 36 shown in FIG. 6 or 7 to convert the signal into the concentration of the magnetic particles.

The concentration measuring unit 36 of the magnetic particle measuring part 2 is connected to the control part 3 for processing of the concentration of the magnetic particles. The control part 3 converts the concentration of the magnetic particles measured by the magnetic particle measuring part 2 into the concentration of hard particles in the oil S by contrast with a calibration line acquired in advance (see FIG. 12) to thereby detect and display the concentration of the hard particles in the oil S. The processes of the control part 3 may be executed manually, the manner of executing the processes being not especially limited.

An operation of the embodiment of the hard particle concentration detecting method according to the invention will be described.

When the fuel or other oil S which may include hard particles is to be tested, firstly a small amount of oil S (sample) for testing is sampled as shown in FIG. 1 from an inlet or the like of the engine in a fuel system (step S1). The fuel or other oil S to be tested is not limited to bunker C or other heavy oil and may be other type of oil S such as gasoline, kerosene or light oil, provided that it may include hard particles. The use of the oil S is not limited to supply to a driving engine of a ship or the like and may be supply to various kinds of driving engines and devices of, for example, a turbine plant. Water or a water solution may be used instead of an oil; the liquid is not especially limited, provided that it may include hard particles. In addition, when water or a water solution is to be tested, the embodiment may be used for detection of particle-like impurities mixed in circulation water of a water circulation compressor or the like, may be used for a water quality inspection of operating water of a hydraulic machine and may be used for water quality management of treated water in a water treatment facility. In addition, hard particles are non-conductive and non-magnetic particles included in a liquid such as the oil S or water and capable of wearing the magnetic member 12 and are not limited to alumina, silica or carbon particles.

Then, the small amount of oil S (sample) sampled is set in the magnetic particle measuring part 2 to measure a concentration (X) of magnetic particles originally included in the oil S (step S2). The processes by the magnetic particle measuring part 2 will be described hereinafter; alternatively, the concentration (X) of the magnetic particles may be measured using other devices. The processes from the sampling of the oil S to setting thereof in the magnetic particle measuring part 2 may be continuously conducted with no manpower through a supplying device such as an oil supply flow path.

After the concentration (X) of the magnetic particles originally included in the oil S is measured, the oil S (sample) is fed into the container 13 which is then set in the magnetic particle producing part 1 for preparation (step S3). More specifically, a spout opening of the container 13 with the oil S therein is fitted over and fixed to the protrusion 14 of the holder 6 such that the magnetic and counterpart members 12 and 11 together with the rod 7 and the like are immersed in the oil S. In any of the other configurations of the magnetic particle producing part 1 shown in FIG. 5, its magnetic and counterpart members are similarly immersed in the oil S. The transfer of the oil S from the magnetic particle measuring part 2 to the magnetic particle producing part 1 may be executed manually or automatically through a transferring device such as a flow path or an on-off valve.

Then, the magnetic particle producing part 1 is driven for a specific time period to produce magnetic particles such as iron powder in the oil S (step S4). More specifically, the drive 5 is driven to rotate the rod 7 and thus the magnetic member 12 while the member 12 is pressed against the counterpart member 11, so that the magnetic member 12 is worn by hard particles entering between the members 12 and 11 to produce magnetic particles due to the wearing of the member 12. In any of the other configurations of the magnetic particle producing part 1 shown in FIG. 5, the magnetic member 12 is similarly worn to produce the magnetic particles such as iron powder. In this step, a viscosity of the oil S is maintained constant so that, when the pressing contact pressure between the members 12 and 11 is kept properly, the magnetic particles (iron powder) are produced only by the hard particles of not less than a specific size. The hard particles of a size smaller than the specific size only pass through a gap between the members 12 and 11 and produce no magnetic particles (iron powder).

After the magnetic particles are produced in the oil S by the magnetic particle producing part 1, the oil S is set from the magnetic particle producing part 1 to the magnetic particle measuring part 2 for the next process. The transfer of the oil S from the magnetic particle producing part 1 to the magnetic particle measuring part 2 may be executed manually or automatically through a transferring device such as a flow path or an on-off valve.

Then, a concentration (Y) of the magnetic particles is measured by the magnetic particle measuring part 2 (step S5). For measurement of the concentration (Y) of the magnetic particles, the piston 39 of the fluid lead-out/lead-in guide unit 33 is continuously reciprocated to alternately and continuously repeat measuring processes with the oil S being introduced into and discharged from the detector body 38. The AC signal transmitting circuit 50 or the like detects a differential signal from output values for the concentration of the magnetic body and for comparison, executes a moving averaging process and acquires an average value of the concentration of the magnetic particles through the concentration measuring unit 36.

Figure 9:
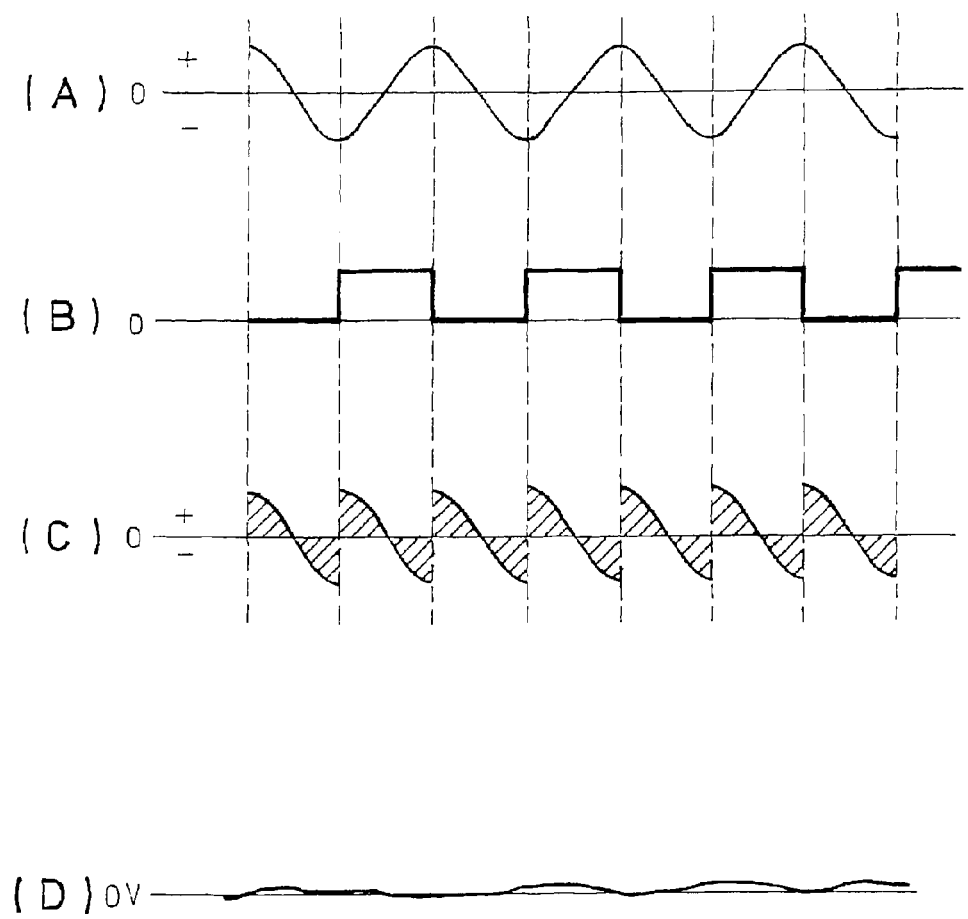
FIG. 9 is a conceptual diagram of processes from an output signal to an output value for comparison under no influence of magnetic particles.
Figure 10:
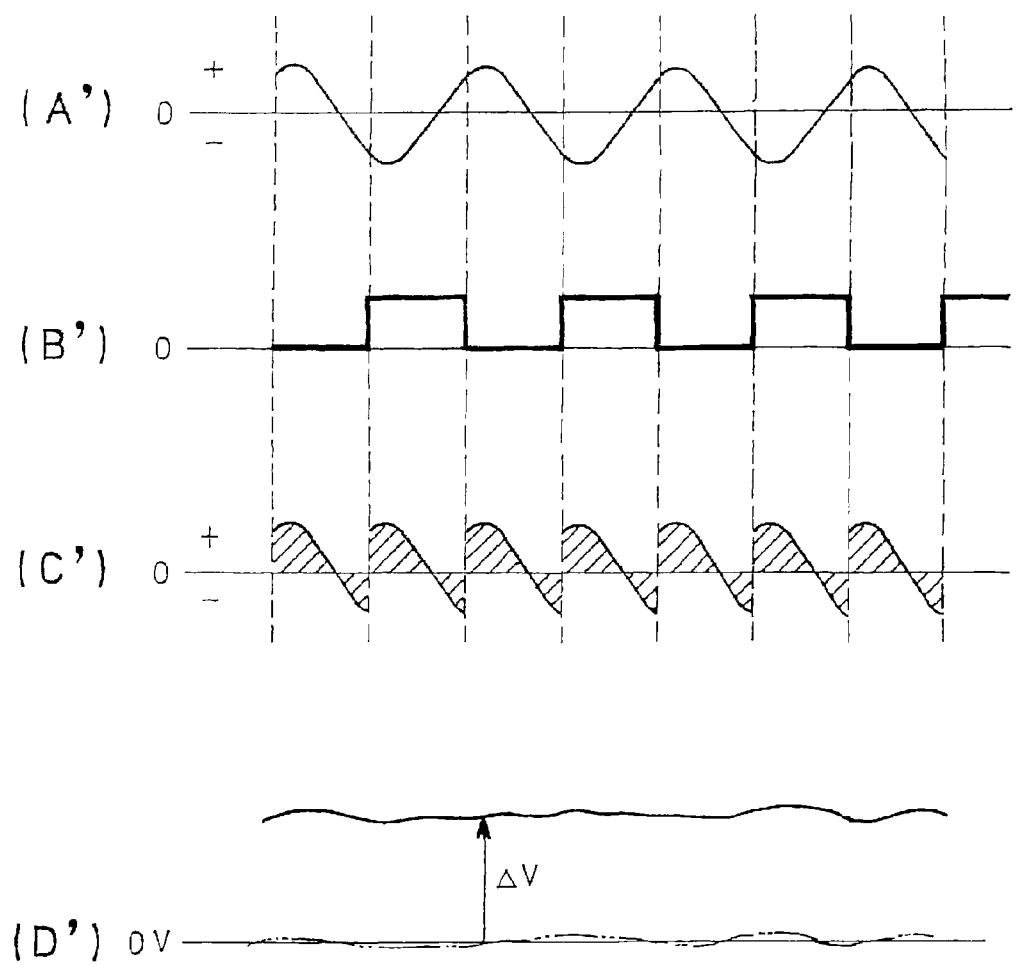
FIG. 10 is a conceptual diagram of processes from the output signal to an output value for a concentration of magnetic particles under the influence of the magnetic particles.

The process of measuring the concentration of the magnetic particles will be described in detail. When the oil S is discharged from the detector body 38, the corrective detection signal is acquired ((A) in FIG. 9) from the detector body 38 through the detection coil 41b, the amplifier circuit 42 and the band-pass filter 43 while the exciting coils 41a, the sine wave oscillating circuit 44, the phase circuit 45 and the edge-trigger circuit 46 are used to prepare, through a phase shift by a predetermined angle, a rectangular-wave reference signal which is at a same frequency as that of the exciting voltage and which generates a specific phase difference relative to the exciting voltage ((B) in FIG. 9 with a phase shift of about 90°). The signal processor 47 executes noise removal for the corrective detection signal together with the reference signal, and detects the phase difference between the corrective detection signal and the reference signal. The low-pass filter 48 converts the phase difference into a smooth DC voltage signal as the output value for the comparison ((D) in FIG. 9) which is input through the amplifier 49 into the AC signal transmitting circuit 50. On the other hand, when the oil S is introduced into the detector body 38, a detection signal of the magnetic body is acquired ((A') in FIG. 10) from the oil S through the detection coil 41b, the amplifier circuit 42 and the band-pass filter 43 while the exciting coils 41a, the sine wave oscillating circuit 44, the phase circuit 45 and the edge-trigger circuit 46 are used to prepare, through a phase shift by a predetermined angle, a rectangular-wave reference signal which is at a same frequency as that of the exciting voltage and which generates a specific phase difference relative to the exciting voltage ((B') in FIG. 10 with a phase shift of about 90°). The signal processor 47 executes noise removal for the detection signal together with the reference signal, and detects the phase difference between the detection signal of the magnetic body and the reference signal. The low-pass filter 48 converts the phase difference into a smooth DC voltage signal as the output value for the concentration of the magnetic body ((D') of FIG. 10) which is input through the amplifier 49 into the AC signal transmitting circuit 50. To correct the output value for the concentration of the magnetic particles, the AC signal transmitting circuit 50 acquires a difference ΔV from the output values for the concentration of the magnetic particles and for the comparison as shown in FIG. 10. The concentration measuring unit 36 converts the difference into the concentration of the magnetic particles based on a correlation (function process) acquired in advance between the difference and the concentration. (C) of FIG. 9 shows a state where the detection signal of the magnetic particles is inverted by the reference signal and conceptually shows that (D) of FIG. 9 is acquired by processing the area thereof by integration. (C') of FIG. 10 shows a state where the detection signal of the magnetic particles is inverted by the reference signal and conceptually shows that (D') of FIG. 10 is acquired by processing the area thereof by integration.

Results of experiments conducted by the inventors reveal that, when the oil S including magnetic particles (iron powder) in ppm was measured using the embodiment, an output (concentration) was increased simultaneously with inputting of the oil S and was decreased in association with discharge of the oil S. It was evident that the reaction of the embodiment against the magnetic particles was clear and quick and the concentration of the magnetic particles was able to be precisely measured.

After the concentration of the magnetic particles is measured by the magnetic particle measuring part 2, the concentration (X) of the magnetic particles originally included in the oil S is subtracted from the concentration (Y) of the magnetic particles acquired after the processing by the magnetic particle producing part 1 (the concentration (Y) of the magnetic particles—the concentration (X) of the magnetic particles) to thereby calculate the concentration (Z) of the magnetic particles actually produced by the magnetic particle producing part 1 (step S6).

Figure 11:
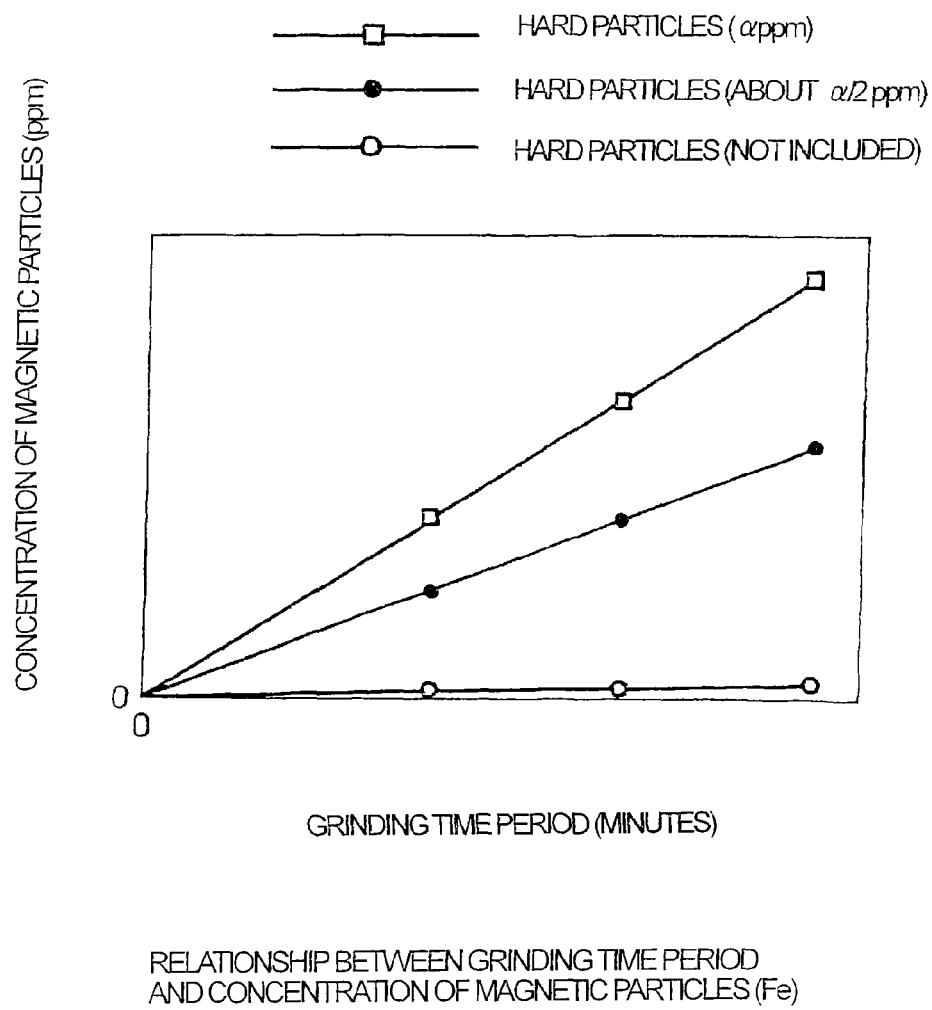
FIG. 11 is a graph showing a relationship between a driving time period (grinding time period) and a concentration of magnetic particles (magnetic powder Fe) in the magnetic particle producing part.
Figure 12:
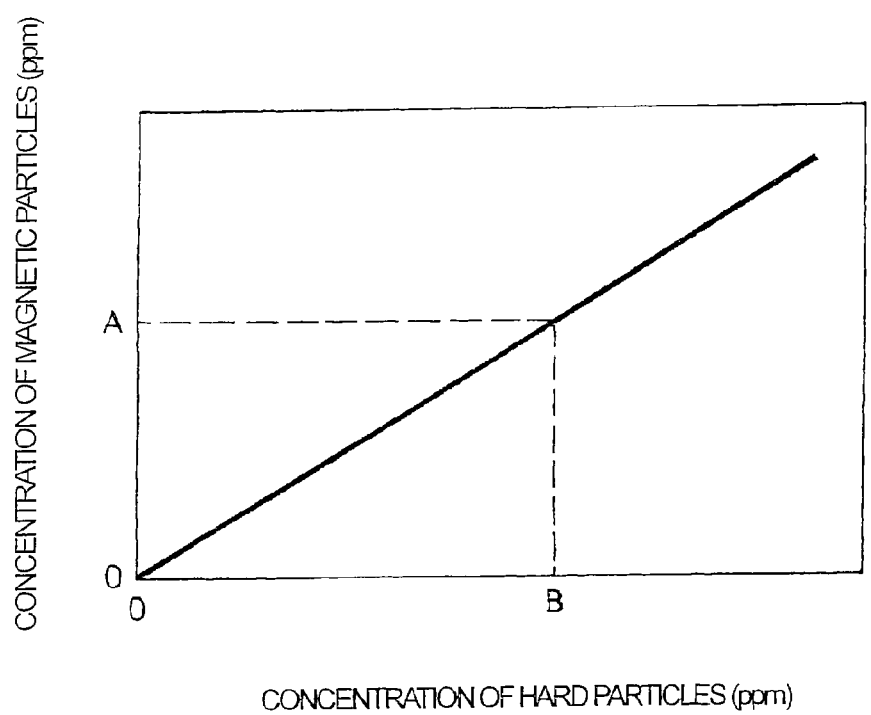
FIG. 12 shows a calibration line representing a relationship between concentrations of hard particles and of the magnetic particles (magnetic powder).

Testing of a relationship between the driving time period (grinding time period) of the magnetic particle producing part 1 and the concentration of the magnetic particles (magnetic powder Fe) revealed that the concentration of the magnetic particles in the oil S linearly increased with elapse of the grinding time period as shown in FIG. 11. With the concentration of the hard particles originally included in the oil S being varied (cases of α ppm, about α/2 ppm and no inclusion are shown in FIG. 11), it turned out that the concentrations of the hard particles and of the magnetic particles produced were in a proportional relationship. Based on this, when the concentrations of the hard particles and of the magnetic particles (magnetic powder) are plotted under the condition that the driving time period (grinding time period) of the magnetic particle producing part 1 is set to be a specific time period, a calibration line was drawn which represented the correlation between the concentrations of the magnetic particles and of the hard particles in the oil S as shown in FIG. 12. The calibration line is applied to the following processes.

After the concentration (Z) of the magnetic particles actually produced is calculated, the concentration of the magnetic particles is converted into the concentration of the hard particles in the oil S based on the calibration line (step S7, from A to B in FIG. 12). The conversion into the concentration of the hard particles may be processed after the calibration line is registered in advance in the control part 3 or may be processed manually.

The concentration of the hard particles is displayed on a displaying unit of the control part 3 or the like (step S8) to thereby detect and quickly and quantitatively grasp the hard particles in the oil S. Thus, the concentration of alumina, silica or other hard particles is determined on site during supply of fuel or other oil S to a driving engine of a ship or the like and any adverse effect to the driving engine caused by the hard particles is prevented in advance.

Thus, according to the embodiment of the hard particle concentration detecting method of the invention, the magnetic particles are produced by wearing the magnetic member 12 due to the presence of the hard particles in the oil S; the concentration of the magnetic particles produced in the oil S is measured; the concentration of the magnetic particles is converted into the concentration of the hard particles in the oil S based on the calibration line to detect the concentration of the hard particles included in the oil S. Thus, a specific number of days are not necessary to detect the concentration of the hard particles unlike the conventional measuring method, and the hard particles in the oil S can be quickly and quantitatively grasped. Therefore, the states can be prevented where untested fuel is used and where a large amount of hard particles are suddenly supplied to a driving engine. Thereby, any adverse effect on the driving engine can be suppressed. The concentration of the hard particles is indirectly detected using the magnetic particles such as iron powder produced by the wearing of the magnetic member 12, so that any operation and any process for direct detection of the hard particles by physically or chemically treating or processing the oil S itself are not required and favorably the hard particles in the oil S can be grasped quickly and quantitatively.

In the embodiment of the hard particle concentration detecting method of the invention, movement of at least one of the magnetic and counterpart members 12 and 11 to the other while pressed to the other and with the hard particles in the oil S being between the members 12 and 11 causes the magnetic member 12 to be properly worn out due to the presence of the hard particles in the oil S to thereby produce the magnetic particles. Thus, the concentration of the hard particles in the oil S can be easily detected to more favorably grasp the hard particles in the oil S.

When an invading path such as the groove 12$a$ is arranged for at least one of the magnetic and counterpart members 12 and 11 for facilitated entering of the sample oil into the gap, it promotes the production and discharge of the magnetic particles (iron powder), whereby the magnetic particles are favorably produced. Thus, the concentration of the hard particles in the oil S can be easily detected and the hard particles in the oil S can be more favorably grasped.

The embodiment can be applied not only to oil but also to water and a water solution. Therefore, the embodiment is highly versatile and can easily detect the concentration of the hard particles from water or a water solution.

It is to be understood that a hard particle concentration detecting method of the invention is not limited to the above illustrated embodiment and that various changes and modifications may be made without departing from the scope of the invention.

REFERENCE SIGNS LIST

1 magnetic particle producing part
2 magnetic particle measuring part
11 counterpart member
12 magnetic member
S oil (liquid)

The invention claimed is:

1. A hard particle concentration detecting method comprising:
    immersing magnetic and counterpart members in a liquid which may include hard particles;
    moving at least one of the magnetic and counterpart members while the at least one member is pressed to the other member;
    wearing the magnetic member by hard particles in the liquid to produce magnetic particles in the liquid;
    measuring a concentration of the magnetic particles produced; and
    converting the measured concentration of the magnetic particles into a concentration of hard particles in the liquid on the basis of a calibration line representing a correlation measured in advance between the concentrations of the magnetic particles and of the hard particles in the liquid to thereby detect the concentration of the hard particles in the liquid.

2. The hard particle concentration detecting method as claimed in claim 1, wherein said at least one of magnetic and counterpart members is moved while pressed to the other member and with the hard particles in the liquid being between the members.

* * * * *